United States Patent [19]
Berger et al.

[11] Patent Number: 5,739,904
[45] Date of Patent: Apr. 14, 1998

[54] METHOD OF OPTICALLY MEASURING THE SURFACE OF YARN PACKAGES

[75] Inventors: Gerald Berger; Jorg Oulabi, both of Wuppertal, Germany

[73] Assignee: Barmag AG, Remscheid, Germany

[21] Appl. No.: 824,076

[22] Filed: Mar. 24, 1997

Related U.S. Application Data

[63] Continuation of Ser. No. 500,775, Jul. 11, 1995, abandoned.

[30] Foreign Application Priority Data

Jul. 11, 1994 [DE] Germany ............... 44 24 038.4

[51] Int. Cl.⁶ .................................................. G01N 21/00
[52] U.S. Cl. ........................................ 356/238; 356/431
[58] Field of Search .................................. 356/238, 426, 356/398, 394, 375, 376, 429, 430, 431

[56] References Cited

U.S. PATENT DOCUMENTS

| | | | |
|---|---|---|---|
| 3,667,846 | 6/1972 | Nater et al. | 356/445 |
| 4,589,773 | 5/1986 | Ido et al. | 356/376 |
| 4,866,289 | 9/1989 | Kawamura et al. | 356/238 |
| 5,138,151 | 8/1992 | Inada et al. | 356/376 |
| 5,224,172 | 6/1993 | Masai | 356/430 |
| 5,315,366 | 5/1994 | Inada et al. | 356/238 |

FOREIGN PATENT DOCUMENTS

| | | |
|---|---|---|
| 0 583 092 | 2/1994 | European Pat. Off. |
| 39 41 008 | 6/1990 | Germany. |
| 42 11 985 | 10/1992 | Germany. |
| B 15741/2151 | 10/1993 | Germany. |
| 36 44 957 | 4/1994 | Germany. |
| A5-78013 | 3/1993 | Japan. |
| 75 104 754 | 2/1988 | Taiwan. |
| 75 105 126 | 3/1988 | Taiwan. |

OTHER PUBLICATIONS

*Denfensive Publication*, "Radiation Sensitive Apparatus for Detecting Rotating Yarn Package Defects", G.L. Buckson et al, published Apr. 29, 1969, 4 pages.

Barmag Electronic brochure; dated Feb. 2, 1994; 2 pages.

Barmag Electronic brochure; dated Feb. 15, 1994; 2 pages.

*Automatic Package Analysis;* Lawson–Hemphill Sales, Inc.; 2 page brochure.

"Triangulationssensor zur hochgenauen Messwertaufnahme an technischen Oberflächen"; Sensor 93 Kongressband III; P. Pfeifer, P. Sowa; Fraunhofer–Institut für Produktionstechnologie IPT, pp. 227–235.

Barmag, "Automatic Package Inspection"; Subheading: Detection of Sloughs; Documentation: Introduction of the Measuring Technique; Proof of Feasibility; Second draft; Copyright G. Berger, Jul. 11, 1994; pp. 1–32.

*Primary Examiner*—Hoa Q. Pham
*Attorney, Agent, or Firm*—Bell Seltzer Intellectual Property Law Group of Alston & Bird LLP

[57] ABSTRACT

A method of optically measuring the surface of yarn packages, wherein the package surface is scanned by a light beam, and the reflected light signal is evaluated. The light beam scans the package surface along a predefined path. At each predetermined measuring time, the light beam is directed to a scanning spot of the package surface, and the two plane coordinates of the scanning spot are determined. A portion of the light rays diffused from the scanning spot is focused and directed to a sensor, so that they arrive at the sensor in one point of incidence. The actual position of the point of incidence is measured, and from the difference between the actual position of the point of incidence and the desired point of incidence, the actual third, i.e. elevation, coordinate of the scanning spot may be determined.

11 Claims, 3 Drawing Sheets

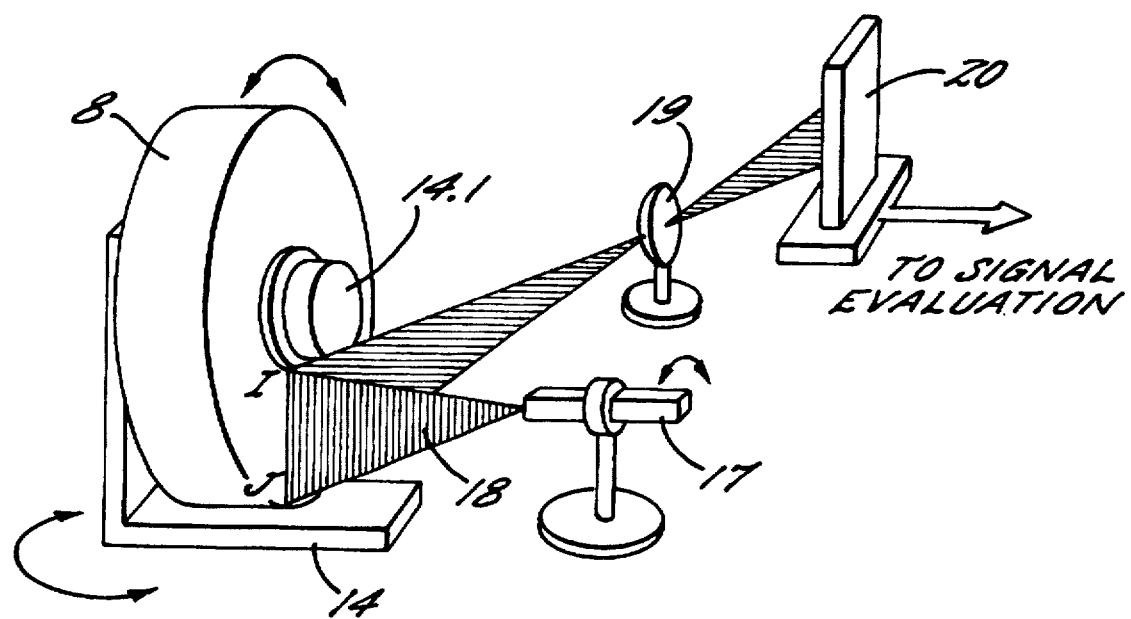
_fig.4._

METHOD OF OPTICALLY MEASURING THE SURFACE OF YARN PACKAGES

This application is a continuation of application Ser. No. 08/500,775, filed Jul. 11, 1995, now abandoned.

BACKGROUND OF THE INVENTION

The invention relates to a method of optically measuring the surfaces of yarn packages.

German Published Application DE 42 11 985 discloses a method of monitoring the form of the wind on yarn packages wherein suction air is applied to the packages to be tested, while they are being transported on package carriers to several package testing devices. The devices that are used for testing the form of the package wind are arranged in a dark chamber. More specifically, the following testing equipment is accommodated in the dark chamber:

Above the upper front end of the package:

1. A fold testing device for examining the presence or absence of folds;

2. A testing device for examining the presence or absence of a yarn segment extending across the end surface;

3. A testing device for examining the presence or absence of a streaked or ribbon wind;

4. A testing device for examining the presence or absence of different yarn types;

At the lower front end of the package:

5. A testing device for yarn segments extending across the end surface in the outer periphery; and 6. A testing device for yarn segments extending across the end surface in the inner periphery.

Further proposed in DE 42 11 985 is a method of projecting a light onto the surface of a package and absorbing the light reflected from the surface by a light-receiving device. The data obtained are examined in an analyzer. Prior to this step of testing the package, the surface of the package is subjected to a suction air current of a suction head.

DE 42 11 985 discloses a method of projecting light in a radial direction onto the end surface of a package being tested, while the package is being rotated by a carrier. In so doing, a linear CCD sensor detects that light which is reflected by yarn segments extending across the end surface of the package and by overlying yarn segments. The data supplied by the linear CCD sensor and resulting from the rotation of the package are binary-coded by a binary code circuit and further processed in a computation circuit, the computation circuit computing the shape of a parabolic curve, which was acquired by the binary-coded circuit, and supplying the computed value to a comparison circuit for comparing this value with a predetermined value.

While the methods proposed in DE 42 11 985 may be suitable for packages of natural yarn, inasmuch as the fiber fly occurring during the processing of these yarns is prevented by the suction air current from contaminating the optical package testing devices that are used in this method, they have however several disadvantages. In particular, the measuring of the package surface requires, on the one hand several (up to six) testing devices, which makes the method costly and expensive.

All optical measuring methods as proposed in DE 42 11 985 are based on measuring the intensity of the reflected light. In this process, it is expected to obtain an especially strong reflection by the skillful illumination of yarn segments extending across the end surface. Such yarn segments extending across the end surface are defects which lessen the quality of a package considerably. However, when applying the proposed methods, the problem arises that overlapping superimposed layers of yarn, in particular superimposed yarn layers overlapping each other continuously in a random manner, are occasionally rated as a yarn segment extending across the end surface. Since this gives rise to judging a satisfactory package as defective, it is necessary to have the inspection personnel conduct a final control which involves a visual inspection.

In addition, in the case of highly glossy, synthetic fibers, which are highly reflective, the methods proposed in DE 42 11 985 do not provide a solution to the problem of automatically measuring packages in the meaning of a quality control.

A method similar to that disclosed in the above-cited German Application is described in U.S. Defensive Publication No. 751,276, by which at least two parallel strips of light are projected onto the end surfaces of a package being tested. The light reflected from the end surface is received by a photodetector, which measures fluctuations in the intensity of the reflection. From the thus-obtained data, defects in the package formation on the end surfaces of the package are detected by comparing the data with predetermined values. Likewise, this method is dependent on the reflection characteristics of the yarn on the package.

Known from JP-A 5-78013 is a method of testing a yarn segment (yarn reserve) wound on a tube outside of the actual range of traverse, wherein for the testing the package is first isolated from external light by means of a black curtain in a type of dark chamber. Thereafter, a light with a wave length close to ultraviolet (180–400 nm) is projected onto a region of the winding tube, in which region the yarn reserve is to be wound. Should the ultraviolet light fall on yarn, the ultraviolet light will excite the molecules of the yarn. At the transition from the excited state to the basic state, the molecules will emit a light in the visible range (400–700 nm). An image detector having a sensitivity adequate to be in the visible range receives the emitted light and converts same into an electrical signal, which is supplied to a signal processor. The signal processor then determines the point on the winding tube, where the yarn reserve was wound and cut. This method is based on the general idea that the molecules of the yarn are excited by the projected ultraviolet light so as to emit a radiation, which differs from that radiation which emanates from the winding tube. It can thus be detected, whether and at which point of the winding tube a yarn reserve was wound and whether and where the yarn was cut. Additional indications of the quality of the package, in particular of its peripheral and end surfaces, cannot be obtained by this method. Likewise, it is not possible by this method to test a yarn reserve that is formed on the wound peripheral surface of the package at the end of a winding cycle.

TW 75 104 754 discloses an optical measuring device for measuring the distance between a surface and a reference plane. This measuring device is based on a method of directing a bundle of rays perpendicularly to the surface being measured. The light rays reflected from the surface are projected by a lens system likewise perpendicular to the surface, and a radiation blocking element with a radiation window is located between the two lenses, so that a certain image forms on the detector surface. The distances between the reference plane and lens system and between the detector and the lens system are equal to the focal length of the lenses, so that the extension of the image on the detector surface represents a measure for the distance between the surface and the reference plane.

The above method has the disadvantage that diffusions that are caused by surface unevennesses, lead to image distortions and can result in faulty measurements. A further source of errors lies in the exact alignment of the measuring device with the reference plane. Taking into account the structure of the package surface, which may include bulges, saddles, loops, lint, and filament breakages, the measuring device disclosed in TW 75 104 754 does not allow to detect sloughs.

TW 75 105 126 discloses a device for optically measuring surface profiles. In the underlying measuring method, a light beam is deflected on a mirror oscillating about its center axis, so that the light beam enters into a lens system and is deflected substantially perpendicularly to the surface to be measured. Arranged along the optical axis between the mirror and the lens system is a radiation divider, which projects the beams reflected from the surface onto a position detector. A light beam varying in its direction allows a constantly changing radiation spot to be projected onto the surface of the position detector. The position detector generates an oscillating output signal, the amplitude of which is evaluated as a measure for the distance between a reference surface and the surface. The distances between the reference surface, the mirror, and between the position detector and the lens system are each equal to the focal lengths of the lens system. Likewise, in this method, unavoidable image distortions resulting from diffusions can lead to serious measuring errors. The proposal to add to the measuring device a second detector in the case of unknown surface roughnesses leads to a complex measuring device without totally eliminating the disadvantage. The exact positioning of the measuring device relative to the reference surface is likewise a disadvantage.

It is therefore the object of the present invention to provide a method of measuring package surfaces, which is substantially independent of the reflection properties of the wound yarn, which can be realized with simple and inexpensive means, which can be universally employed, in particular also in rooms with standard lighting and without shielding a package being examined in a dark chamber, namely, which is suitable for measuring the two end surfaces and the peripheral surface including the surfaces on the winding tube, on which no yarn or only little yarn is wound by traversing, and which requires only little time for measuring a package.

SUMMARY OF THE INVENTION

The above and other objects and advantages of the present invention are achieved by the provision of a method of optically measuring the surface of yarn packages, wherein the package surface is scanned by a light beam and the reflected light signal is evaluated, and with the light beam scanning the package surface along a predefined scanning path. The method is characterized by the steps of directing at each predetermined measuring time the light beam to a scanning spot on the package surface and so as to determine the two plane coordinates (x, y) of the scanning spot, determining the desired elevation coordinate (z) of the scanning spot, and focusing a portion of the light rays diffused from the scanning spot, and directing same to a surface sensor, so that they arrive at the surface sensor in one point of incidence. The surface sensor then measures the actual position of the point of incidence on the surface sensor, and the determined two plane coordinates (x, y) and the desired elevation coordinate (z) of the scanning spot are associated to the point of incidence for determining its desired geometric position. The difference between the actual position and the desired position of the point of incidence is determined, and the actual elevation coordinate of the scanning spot is determined therefrom.

The method has the advantage that all kinds of yarn packages can be measured, in particular even those comprising textured or untextured synthetic yarns. The term "yarn" as used herein includes all filiform textile structures, in particular monofilaments which consist of only one filament, multifilament yarns which consist of a plurality of filaments, as well as slit-film yarns which have the shape of a flat or twisted film.

The method has the further advantage that the measured data can be evaluated by many different criteria as are predetermined by the user, and that they are especially suitable for determining the different quality parameters.

The light beam scanning the package may be generated by means of a laser, the advantage of so doing is that by applying known devices (for plane-parallel mirrors), the laser wave bundles itself, whereas the individual particles of a thermal radiator basically radiate omnidirectional spherical waves. This results in the best approximation to a parallel bundle, which can actually be realized, when taking into account the wave nature of the light. Thus, the finite extension of a thermal light source can always be contracted only to one image, the size B of which results from the equation $B=Gb/g$, i.e. the relation between the image distance (b) and object distance (g) as well as the object size G. If b were made very large and thus B very small, the imaging system would receive only little power, since the intensity of the spherically reflected rays decreases quadratically with their increasing distance from the source of light. In comparison therewith, a laser with its strictly parallel bundle can be conceived as a practically infinitely remote light source, g thus being infinite, and the image size B becoming thus geometric-optically infinitely small. Since, in this instance, the intensity of the light does practically not decrease, this means that with the use of a laser for generating the light beam the optical resolving power of the method can be so great, as to still allow the measuring of structures which are smaller than the diameters of the finest existing yarns.

Depending on the kind, weight, and size of the packages being examined, and depending on the space available for the application of the method, it may be especially practical to lay out the scanning path to be in the form of a spiral or a plurality of straight lines. Accordingly, the form of the scanning path results always from the relative movement of the light beam and package, i.e., either the light beam is moved, for example, by means of a deflecting mirror, or the package, or both are moved.

Depending on what the user wants to know about the package as a result of measuring the surface of the package, it may be practical to compose an elevation profile from the detected elevations of the individual scanning spots on the package surface. The term "elevation profile" as used herein is understood to be a three-dimensional matrix, in which for each scanning spot of the examined surface three independent space coordinates of the scanning spot are determined, so as to be able to indicate heights and depths on the surface of the package.

The present invention may also include a comparison of the determined elevation profile with an ideal profile for determining a quality parameter. This provides the advantage that the quality analysis of the package, which has until now been carried at great expense by inspection personnel, can now occur fully automatically. It is now possible to rate the yarn packages being examined by different quality criteria. In particular, the method makes it also possible to recognize so-called "sloughs." Sloughs are those portions of the yarn which have slipped from their actual position on the package periphery to the end surfaces of the package, and extend now, in the fashion of a chord, across the end surface of the package. In the instance of very fine yarns, the detection of sloughs has so far set exacting requirements on the visual power of the person performing the inspection, and it strains the person's vision due to a high light intensity, which leads to a rapid fatigue of the eyes. However, as described further below, the proposed method allows likewise other criteria to be examined for rating the quality of a package.

The method of the present invention may also include the further steps of measuring the intensity of the incident light by means of a sensor, associating to each scanning spot the intensity of the light reflected therefrom, and determining from the entirety of the scanning spots a profile of the reflection power of the package surface. Also, the profile of the reflection power may be compared with an ideal profile so as to permit the quality parameters of the package to be determined. When the method is applied in accordance with these steps, it will be possible to obtain further indications of the package surface being measured, since, for example, oil spots on the package or changes in the polymer normally show in a change of the reflection power of the yarn.

The light beam which scans the surface of the winding tube may scan along a predetermined path so that an elevation profile of the winding tube is produced, which may then be compared with an ideal profile of the winding tube so as to determine a further quality parameter. This step provides a simple and fast inspection, whether, and if so, where a yarn reserve was wound on the winding tube.

The method of the present invention may also use the determined quality parameters for controlling the textile machine that produces the package, since the proposed measuring method operates very fast. When applied directly to freshly produced packages, it will be possible, should be packages exhibit quality defects, to readjust the package producing textile machine accordingly.

BRIEF DESCRIPTION OF THE DRAWINGS

Further details and advantages of the invention will become apparent when considered in conjunction with the following schematic illustrations, in which

FIG. 4 illustrates the application of the method, wherein the light beam is focused to a line prior to its incidence upon the package.

DETAILED DESCRIPTION OF THE PREFERRED EMBODIMENTS

Figure 1:
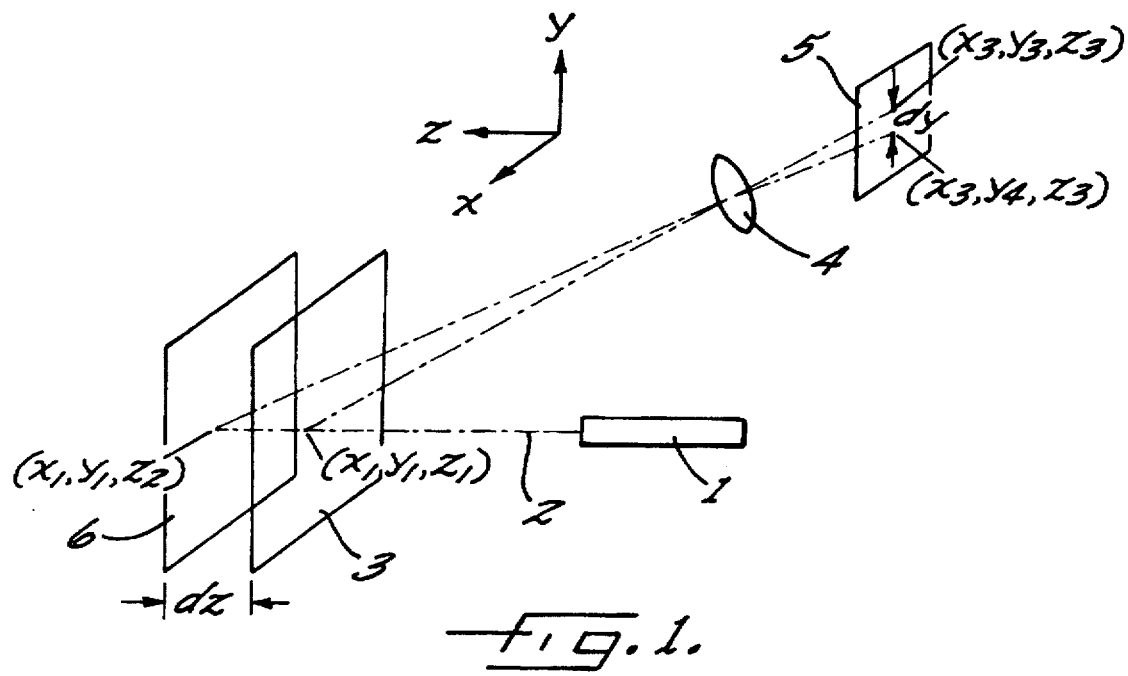
FIG. 1 is a diagram illustrating the basic principle of the method of the present invention.

FIG. 1 illustrates the basic principle of the measuring method. A light source 1 produces a light beam 2 indicated by a dash-dotted line. This light beam 2 arrives in a first plane 3 at a point with the coordinates $(x_1, y_1, x_1)$, where it is diffused. A portion of the diffused rays are focused by a lens 4 in a point and directed to a surface sensor 5, so that they arrive at the surface sensor 5 in one point with the coordinates $(x_3, y_3, z_3)$. However, should the light beam 2 arrive at a point having the coordinates $(x_1, y_1, z_2)$, which is located in a second plane 6 removed in depth by a distance dz from the first plane 3, the light that is diffused from this point is focussed by lens 4 and directed to the surface sensor 5, so that it falls on the surface sensor at a point $(x_3, y_4, z_3)$. This means that a change in the depth z reflects in a change of the points of incidence on the surface sensor (in the arrangement selected for illustrating the principle, a shift of the points causing the reflection by dz reveals itself in a displacement of the points of incidence by dy). From the position of the points of incidence on surface sensor 5, it will be possible to determine directly the location of the scanning spot causing the reflection, when the light source, scanning spot, and sensor are arranged in a triangle.

Figure 2:
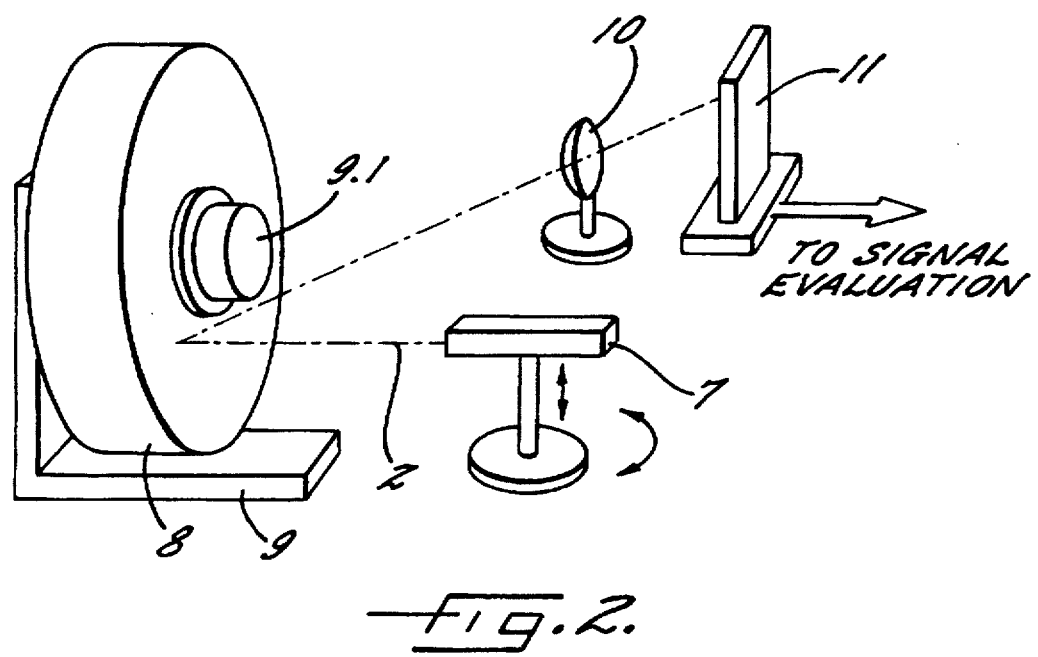
FIG. 2 illustrates the method of focusing a portion of the reflected light in a point on a surface sensor.

In FIG. 2, the light beam 2 is produced by a movable light source 7 and projected onto a package 8 being examined. The package 8 is located on a package carrier 9 that is provided with a mandrel 9.1 for receiving the package. A portion of the diffused light rays is focused to a point by a lens 10 and directed to a surface sensor 11. From the position of the movable light source 7 relative to package 8 the two plane coordinates (x,y) of the respective scanning spot on the package surface are obtained. The surface sensor 11 measures the actual position of the point of incidence. When the two plane coordinates of the scanning spot are associated to the point of incidence for determining its desired geometrical position, the difference between the actual position and the desired position of the point of incidence permits the determination of the actual elevation coordinate (z) of the scanning spot on the package surface. The surface sensor 11 may be, for example a matrix-type CCD sensor consisting of many individual CCD elements juxtaposed and superposed in one plane.

Figure 3A:
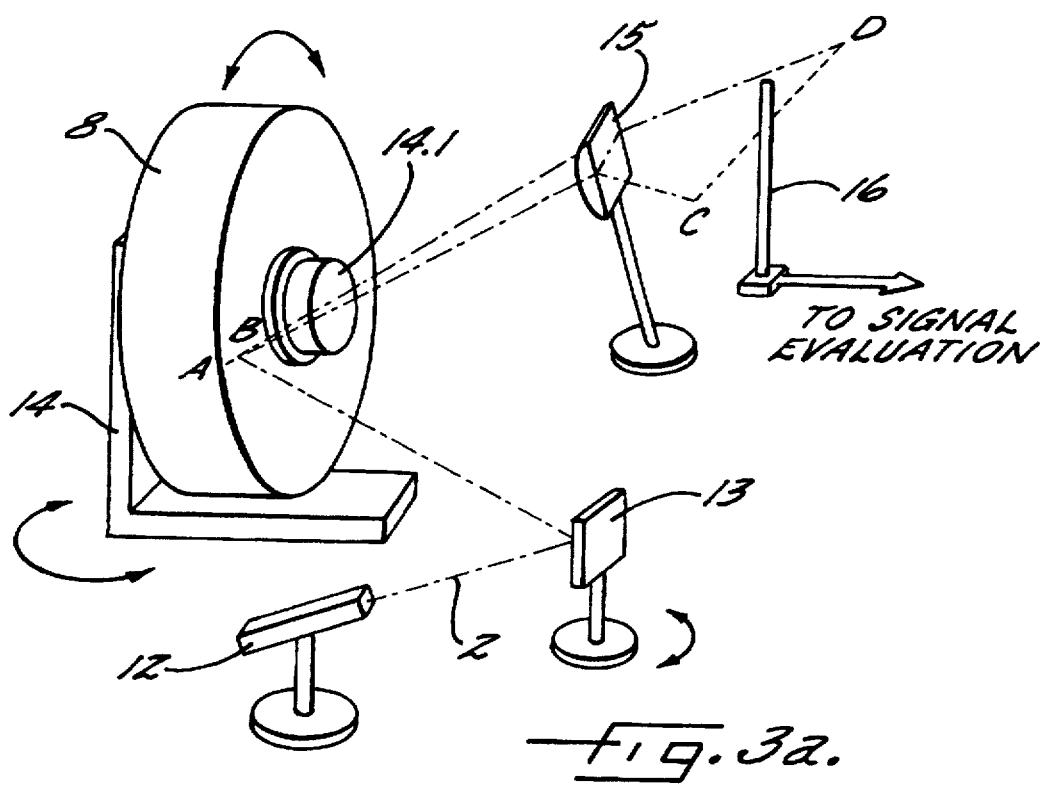
FIG. 3a illustrates the application of the method to an end surface of a package, a portion of the reflected light being linearly focused and directed to a line sensor.
Figure 3B:
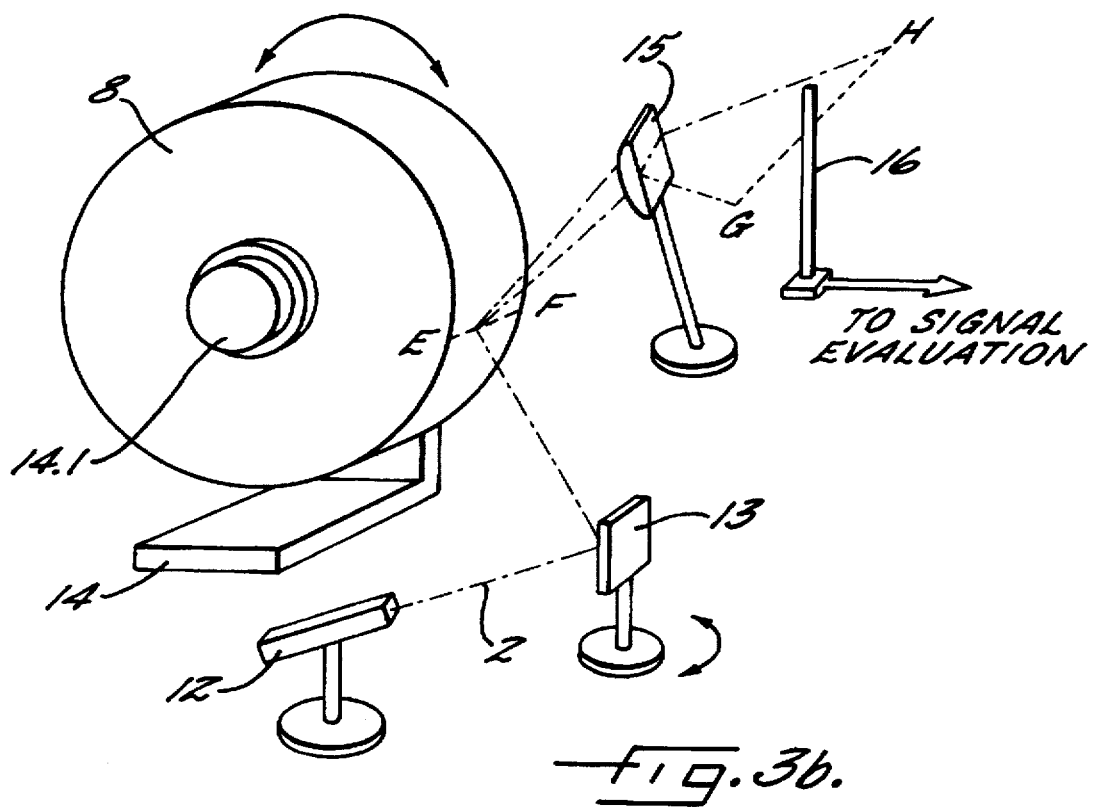
FIG. 3b illustrates the application of the method shown in FIG. 3a to the peripheral surface of the package.

In FIGS. 3a and 3b, the light beam 2 is produced by a stationary light source 12 and projected onto a rotatable mirror 13. The mirror 13 deflects the light beam 2 to different scanning spots along a straight line AB. The package 7 to be examined is rotatably supported on a movable package carrier 14. The package carrier 14 includes a rotatable mandrel 14.1 for receiving package 7. To cover the scanning spots on the entire package surface, different approaches are possible. To begin with, the package is held in its position shown in FIG. 3a, and the light beam 2 is radially deflected onto an end surface of the package along line AB. Once the scanning procedure in this direction is completed, the mandrel 14.1 rotates the package by a distance, and the next line on the end surface of the package is scanned. The rotatable mirror may, for example, be a part of a mirror galvanometer, which distinguishes itself by its high deflection frequency, thus allowing the package to be scanned in the range of seconds at a speed of 1 to 2 revolutions per second. A portion of the light rays diffused from each scanning spot is linearly focused by a cylindrical lens 15 and projected onto a line sensor 16. In the special arrangement shown in FIGS. 3a and 3b, the line CD generated by cylindrical lens 15 intersects line sensor 16 perpendicularly. If the package end surface were absolutely flat, a scanning along the line AB would always cause the cylindrical lens to produce lines CD which extend overlapping each other along a straight line. This means that the line sensor would always measure the same position of the intersection. Since in the proposed method, only a change in elevation on the package end surface being examined is of interest (since the plane coordinates of the scanning spot are already known from the relative position of the rotatable mirror and the package), the cylindrical lens 15 allows to make the method invariant to changes within the known plane. As regards the sensor, a single line of CCD elements is adequate for this method. However, it is also possible to use other types of sensors, for example the so-called PSD (position-sensitive device) sensors. Basically both digital and analog sensors are suitable, which also include photodiodes, photoelements, and photo resistors. When using a photodiode which produces a signal mixture that reproduces simultaneously the distance and the reflection power of the object, it will possible to obtain with the aid of a second photodiode, the so-called compensation diode, which detects only the signal portion corresponding to the reflection power, the cleaned-up location signal by forming the difference of both signals. In FIG. 3b, the package carrier 14 is rotated by 90°, so that the peripheral surface of package 8 can now be measured. To this end, the light beam 2 is deflected by rotating mirror 13 onto scanning spots along a line EF. Each time when the light beam reaches one end of this line, the mandrel 14.1 rotates the package 8 by a distance, and a new scanning process starts.

A particularly rapid variant of the method is shown in FIG. 4. Already integrated in a light source 17 rotatable about its longitudinal axis is a cylindrical lens which diverges the light beam, so that a diverged light beam 18 falls on the package surface being examined along a line IJ. From the position of the light source 17 relative to package 8, the two plane coordinates are obtained for the different scanning spots extending along the line IJ on the package surface. A portion of the light rays diffused from these scanning points is focused by a lens 19 and directed to a surface sensor 20. From the position of the points of incidence on the surface sensor, it is now possible to determine by forming the difference between the actual position and the desired position of the points of incidence the elevations of the respective scanning spots. It is thus possible to simultaneously cover at a single measuring time several scanning points on the package surface. The package 8 is rotatably supported on a rotatable package carrier 14. The package carrier 14 is provided with a mandrel 14.1 for receiving package 8. Once a line on the package surface being examined has been scanned, the mandrel 14.1 rotates the package by a certain distance. Once a package surface, for example, an end surface, has been covered, the package carrier 14 can be rotated by 90°, and likewise the light source 17, so that the previously vertical scanning line extends now horizontally, and that it is now possible to measure the peripheral surface of package 8.

The elevation profile that is obtained by one of the above-described methods, is an objective measure for the quality of the package end surface. The location, and not the luminance of the reflex, on the sensor is a measure for the elevation. Thus, the method is independent of the reflection characteristics of the package being examined. However, the intensity of the reflected light may also be measured by the sensors and be associated to the respective scanning points. Thus, it becomes possible to measure different quality parameters of the package, such as, for example, contaminations and changes in the polymer. When the measured elevations of the scanning points are combined to an elevation profile of the package surface, it will be possible to determine from a comparison of this actual profile with a desired profile the different quality parameters of the package. Thus, for example, the previously described sloughs become apparent in a linear elevation on the end surface of the package. Other characteristics of the package, which can be measured by the proposed method, include, for example, a saddle, bulge, loops, lint, and filament breakages. The term "saddle" as used herein represents a low point toward the center of the peripheral surface of the package. The term "bulge" is understood to be a protrusion of an end surface of the package. Loops can form on the end and peripheral surfaces of the package, and they are yarn lengths that are not tautly wound and project like loops from the package. Depending on the type of the wound yarn, lint may form during the winding process which, as it whirls around, is caught and wound along with the yarn being wound.

With special advantage, the method may thus be used for automatically determining the quality parameters of the package. The resultant quality parameters can easily be stored on a data carrier which is attached to the package. Thus, the packages are ready for packaging. However, the determined quality data may be used likewise very advantageously for controlling the machinery producing the packages, since the proposed methods are capable of determining the quality parameters of the package very rapidly. If the methods are applied, directly after producing the packages to the just finished packages, it will be possible to identify defects on the packages very fast and to readjust the machinery accordingly.

In the drawings and the specification, there have been set forth preferred embodiments of the invention and, although specific terms are employed, the terms are used in a generic and descriptive sense only and not for purpose of limitation, the scope of the invention being set forth in the following claims.

That which is claimed is:

1. A method of optically measuring the surface of yarn packages, wherein the package surface is scanned by a light beam and the reflected light signal is evaluated, the light beam Scanning the package surface along a predefined scanning path, characterized by the steps of directing at each predetermined measuring time the light beam to a scanning spot on the package surface and so as to determine the two plane coordinates (x, y) of the scanning spot;

determining the desired elevation coordinate (z) of the scanning spot;

focusing a portion of the light rays diffused from the scanning spot, and directing same to a surface sensor, so that they arrive at the surface sensor in one point of measuring with the surface sensor the actual position of the point of incidence on the surface sensor and including measuring and evaluating the intensity of the incident light by means of the surface sensor at each of a plurality of scanning spots;

associating the determined two plane coordinates (x, y) and the desired elevation coordinate (z) of the scanning spot to the point of incidence for determining its desired geometric position; and determining the difference between the actual position and the desired position of the point of incidence and determining therefrom the actual elevation coordinate of the scanning spot.

2. The method as defined in claim 1 further characterized by the step of producing the light beam by means of a laser.

3. The method as defined in claim 1 further characterized in that the directing step includes moving the light beam along a plurality of straight lines.

4. The method as defined in claim 1 characterized by the further step of combining a plurality of the determined elevation coordinates to form an elevation profile of the package surface.

5. The method as defined in claim 4 characterized by the further step of comparing the elevation profile with an ideal profile and determining therefrom the quality parameters of the package.

6. The method as defined in claim 1 wherein the measuring and evaluating step includes associating to each scanning spot the intensity of the light reflected therefrom, and determining from the entirety of the scanning spots a profile of the intensity of the light reflected from the package surface.

7. The method as defined in claim 6 wherein the measuring and evaluating step further includes the step of comparing the profile of the intensity of the light reflected from the package surface with an ideal profile and determining therefrom the quality parameters of the package.

8. The method as defined in claim 1 wherein the yarn package includes a winding tube, and wherein the method is characterized in that the light beam scans the surface of the winding tube along a predetermined path and that an elevation profile of the winding tube is produced, and comparing the elevation profile with an ideal profile of the winding tube so as to determine a quality parameter.

9. The method as defined in claim 8 characterized by the further step of using the determined quality parameters for controlling a textile machine that produces the package.

10. A method of optically measuring the surface of yarn packages, wherein the package surface is scanned by a light beam and the reflected light signal is evaluated, the light beam scanning the package surface along a predefined scanning path, characterized by the steps of directing at each predetermined measuring time the light beam to a scanning spot on the package surface and so as to determine the two plane coordinates (x, y) of the scanning spot;

determining the desired elevation coordinate (z) of the scanning spot;

focusing by means of a cylindrical lens a portion of the light rays diffused from the scanning spot to form a light line, end directing same to an elongate line sensor, so that the light line intersects the line-sensor;

measuring with the line sensor the actual position of the intersection of the light line and the line sensor and including measuring and evaluating the intensity of the incident light by means of the surface sensor at each of a plurality of scanning spots;

associating the determined two plane coordinates (x, y) and the desired elevation coordinate (z) of the scanning spot to the intersection for determining its desired geometric position; and determining the difference between the actual position and the desired position of the intersection and determining therefrom the actual elevation coordinate of the scanning spot.

11. A method of optically measuring the surface of yarn packages, wherein the package surface is scanned by a light beam and the reflected light signal is evaluated, the light beam scanning the package surface along a predefined scanning path, characterized by the steps of focusing the light beam to form a line and directing the line to a scanning path on the package surface and so as to determine the two plane coordinates (x, y) of each of a plurality of scanning spots along the line;

determining the desired elevation coordinate (z) of each of the scanning spots along the line;

focusing a portion of the light rays diffused from each scanning spot, and directing same to a surface sensor, so that they arrive at the surface sensor in one point of incidence;

measuring with the surface sensor the actual position of each point of incidence on the surface sensor and including measuring and evaluating the intensity of the incident light by means of the surface sensor at each of a plurality of scanning spots;

associating the determined two plane coordinates (x, y) and the desired elevation coordinate (z) of each scanning spot to the respective point of incidence for determining its desired geometric position; and determining the difference between the actual position and the desired position of the point of incidence and determining therefrom the actual elevation coordinate of each scanning spot.

* * * * *